(12) United States Patent
Brouard et al.

(10) Patent No.: US 9,668,957 B2
(45) Date of Patent: Jun. 6, 2017

(54) COSMETIC COMPOSITIONS

(71) Applicant: Symrise AG, Holzminden (DE)

(72) Inventors: Denis Brouard, Saint Ouen (FR);
Cecile Kalem, Issy-les-Moulineaux
(FR); Martina König, Hamburg (DE);
Sabine Lange, Holzminden (DE); **Sven
Siegel**, Höxter (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/420,045

(22) PCT Filed: Aug. 1, 2013

(86) PCT No.: PCT/EP2013/066171
§ 371 (c)(1),
(2) Date: Feb. 6, 2015

(87) PCT Pub. No.: WO2014/023640
PCT Pub. Date: Feb. 13, 2014

(65) Prior Publication Data
US 2015/0190326 A1 Jul. 9, 2015

(30) Foreign Application Priority Data

Aug. 7, 2012 (EP) .................................... 12 179479

(51) Int. Cl.
| A61K 9/00 | (2006.01) |
| A61K 8/02 | (2006.01) |
| A61K 8/00 | (2006.01) |
| A61K 31/74 | (2006.01) |
| A61K 8/49 | (2006.01) |
| A61K 8/06 | (2006.01) |
| A61K 8/39 | (2006.01) |
| A61Q 15/00 | (2006.01) |
| A61K 8/92 | (2006.01) |
| A61K 8/26 | (2006.01) |
| A61K 8/37 | (2006.01) |
| A61Q 17/04 | (2006.01) |
| A61Q 19/00 | (2006.01) |

(52) U.S. Cl.
CPC ............... *A61K 8/498* (2013.01); *A61K 8/06* (2013.01); *A61K 8/26* (2013.01); *A61K 8/37* (2013.01); *A61K 8/39* (2013.01); *A61K 8/4973* (2013.01); *A61K 8/922* (2013.01); *A61Q 15/00* (2013.01); *A61Q 17/04* (2013.01); *A61Q 19/00* (2013.01); *A61K 2800/244* (2013.01)

(58) Field of Classification Search
None
See application file for complete search history.

(56) References Cited

U.S. PATENT DOCUMENTS

2003/0235545 A1  12/2003  Guenin et al.
2007/0243150 A1  10/2007  Bottiglieri

FOREIGN PATENT DOCUMENTS

WO  2007/094972 A2  8/2007

OTHER PUBLICATIONS

PubChem Entry for menthone glycerol ketal; downloaded Dec. 8, 2012 (15 pp).*
Handbook of Pharmaceutical Excipients; 6th Ed.; (2009); pp. 554-556 for "polyoxyethylene stearates".*

* cited by examiner

*Primary Examiner* — Jeffrey T Palenik
(74) *Attorney, Agent, or Firm* — Dilworth & Barrese LLP

(57) ABSTRACT

Suggested is a cosmetic composition, comprising
(a) menthone compounds according to formula (Ia) or (Ib)

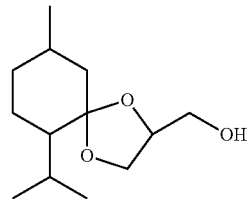

(Ia)

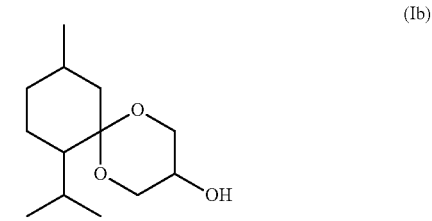

(Ib)

and
(b) at least one oil body or wax, and optionally
(c) at least one emulsifier and/or
(d) at least one active principle 7 Claims, 4 Drawing Sheets Figures 1 a, b and c :

Emulsion with 10% Caprylic/Capric/Triglceride

Comparison of particle size distribution Example 7 (left) vs. Comparative Example C7 (right)

Figures 2 a, b and c:

Emulsion with 10% Cetearyl Ethylhexanoate

Comparison of particle size distribution Example 8 (left) vs. Comparative Example C8 (right)

Figures 3 a, b and c:

Emulsion with 10% Soybean Oil

Comparison of particle size distribution Example 9 (left) vs. Comparative Example C9 (right)

Abrasion of skin: left with Menthone Glyceryl Acetal, right without

Appearance of broken stick: right with Menthone Glyceryl Acetal, left without

COSMETIC COMPOSITIONS

CROSS REFERENCE TO RELATED APPLICATIONS

This application claims priority from International Application No. PCT/EP2013/066171, filed on Aug. 1, 2013.

FIELD OF INVENTION

The present invention belongs to the area of cosmetics and refers to new compositions comprising selected menthone compounds with improved stability and enhanced sensorial profile when applied to human skin.

STATE OF THE ART

Typically, cosmetic compositions comprise a multitude of components. Looking at the listing of ingredients for an average night cream one can find up to 20 positions and there has been a tendency to add as many ingredients as possible in order to address many different issues, all at the same time. As a matter of fact, many consumers equal complexity of a composition with benefit and are accepting high prices, since (s)he expect also high performance. On the other hand, the more complex a composition becomes, the more difficult it is to avoid negative interactions between the components. A major problem for cosmetic compositions, of course in particular for all types of emulsions, is still their stability, especially in case they are subjected to difficult storage conditions, like high or low temperatures.

Another object is related to the sensorial profile. Spreadability, afterfeel and smell are important parameters contributing to the overall liking of a cosmetic formulation after application to skin:

The faster the oil bodies of an emulsion are spread on the skin the better is the perception of the customer. The spreading behaviour of a formulation—and therefore its sensorial profile—is linked to the average particle size of the droplets in the composition. The smaller the droplets are, the faster the spreading is. As a consequence, there is still a need for additives allowing to shift the average particle size distribution to lower values.

Also, bad smell still represents a problem especially for the compositions containing high amounts of fatty materials. Generally formulators need specific combination of fragrances in order to mask the malodour of a cosmetic formulation. However, it could be advantageous to use a new additive addressing this issue while solving simultaneously the other above mentioned problems, in particular spreadability, greasy afterfeel and stability.

Therefore, the object of the present invention has been to identify a multi-functional additive for cosmetic formulations, which does not negatively interact with other ingredients while improving the stability and the sensorial profile of the cosmetic compositions containing this additive.

DESCRIPTION OF THE INVENTION

Figure 1A:
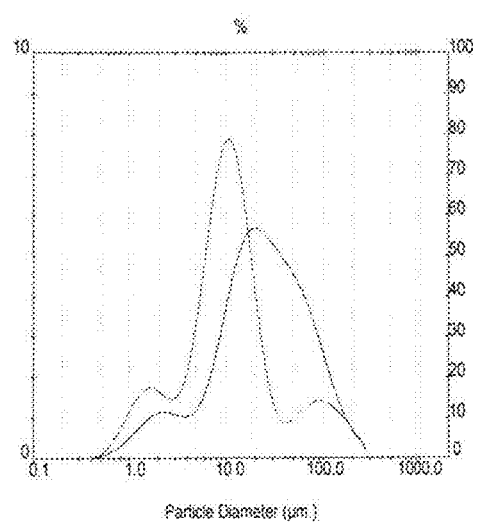
FIG. 1a is a graph of the particle diameter distribution of the emulsion of example 7 and comparative example C7 detailed in Tables 3 and 4.

Object of the present invention are cosmetic compositions, comprising
(a) Menthone compounds according to formula (Ia) or (Ib)

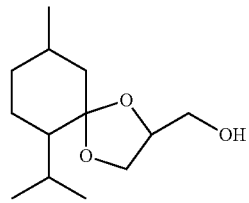

(Ia)

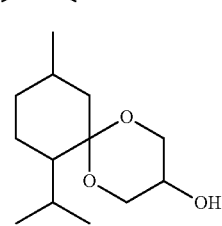

(Ib)

and
(b) at least one oil body (b1) and/or wax (b2), and optionally
(c) at least one emulsifier and/or
(d) at least one active principle Surprisingly it has been observed that the menthone ketals according to the present invention serve all the above mentioned needs simultaneously:

- adjunction of menthone ketals improves the stability of cosmetic formulations even under difficult storage conditions
- at the same time, adjunction of menthone ketals in a cosmetic formulation can help improve its sensorial profile:
  - first of all, menthone ketals are able to provide a cooling sensation to the skin,
  - menthone ketals leads to the formation of smaller droplets in the compositions. Due to the fact the oil or water droplets more finely divided, the sensation on skin is improved. For example, the greasy afterfeel of creams and lotions can be reduced in that way. The deodorants can also have a smoother feeling and a more creamy feeling when applied to the skin;
  - menthone ketals are also able to reduce the malodour of compositions having intrinsic fatty smells.

Therefore, menthone ketals serve the need for so-called "true multi-tasking ingredients".

Menthone Ketals

Menthone ketals (component a) encompass two structures namely L-Menthone Glycerol Acetal/Ketal (FEMA GRAS 3807) and DL-Menthone Glycerol Ketal (FEMA GRAS 3808) and their mixture. FEMA GRAS 3807 is available for example under the trade mark Frescolat® MGA and the INCI: Menthone Glycerin Acetal (Symrise AG) and belongs to a group of menthol derivatives providing a cooling sensation to skin and mucous membranes. The product-is in particular suggested for applications in the areas of oral care, hair care, sun care, skin care, toiletries, pharmaceuticals, laundry and nutrition and in particular for chewing gums and beverages. Originally recommended as a cooling agent for chewing gum by Wrigley Co. (EP 0485170 B1), it is also suggested for non-therapeutic use in cosmetics (EP 0507190 B1, Haarmann & Reimer).

Oil Bodies

Suitable oil bodies (component b1), are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsalv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils.

Waxes

Among the group of suitable waxes (component b2) one can differentiate between the following types:
- superfatting agents
- consistency factors
- pearlising waxes, and
- natural waxes Superfatting Agents.

Superfatting agents may be selected from substances such as for example, lanolin and lecithin and also polyethoxylated or acylated lanolin and lecithin derivatives, polyol fatty acid esters, monoglycerides and fatty acid alkanolamides; fatty acid alkanolamides can also serve as foam stabilizers.

Consistency Factors.

The consistency factors can be for example fatty alcohols or hydroxyfatty alcohols containing 12 to 22 and preferably 16 to 18 carbon atoms and also partial glycerides, fatty acids or hydroxyfatty acids of the same carbon range. A combination of these substances with alkyl oligoglucosides and/or fatty acid N-methyl glucamides of the same chain length and/or polyglycerol poly-12-hydroxystearates is preferably used.

Pearlising Waxes.

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Natural Waxes.

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Emulsifiers

As an optional, the compositions according to the present invention may also include emulsifiers (component c). The emulsifiers may be of non-ionic, anionic, cationic and/or amphoteric nature.

In particular preferred are non-ionic emulsifiers, such as:
  products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
  $C_{12/18}$ fatty acid monoesters and diesters of addition products of 1 to 30 mol ethylene oxide onto glycerol;
  glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The most preferred emulsifiers are described in more detail as follows:

A. Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

B. Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

C. Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellna®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

D. Anionic Emulsifiers

Typical anionic emulsifiers are aliphatic $C_{12-22}$ fatty acids, such as palmitic acid, stearic acid or behenic acid for example, and $C_{12-22}$ dicarboxylic acids, such as aze laic acid or sebacic acid for example.

E. Amphoteric or Zwitterionic Emulsifiers

Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Active Principles

The compositions according to the present invention may contain additional ingredients encompassed by the term "active principles". Examples for suitable ingredients are surfactants, thickeners, polymers, silicone compounds, stabilizers, primary and secondary sun protection agents, antidandruff agents, biogenic agents, film formers, swelling agents, hydrotropes, preservatives, solubilizers, complexing agents, reducing agents, alkalising agents, perfume oils, and dyes A. Surfactants Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineraloladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

B. Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

C. Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohy-droxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

D. Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

E. Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
- p-aminobenzoic acid
- p-aminobenzoic acid ethyl ester (25 mol) ethoxylated (INCI name: PEG-25 PABA)
- p-dimethylaminobenzoic acid-2-ethylhexyl ester
- p-aminobenzoic acid ethyl ester (2 mol) N-propoxylated
- p-aminobenzoic acid glycerol ester
- salicylic acid homomenthyl ester (homosalates) (Neo Heliopan® HMS)
- salicylic acid-2-ethylhexyl ester (Neo Heliopan® OS)
- triethanolamine salicylate
- 4-isopropyl benzyl salicylate
- anthranilic acid menthyl ester (Neo Heliopan® MA)
- diisopropyl cinnamic acid ethyl ester
- p-methoxycinnamic acid-2-ethylhexyl ester (Neo Heliopan® AV)
- diisopropyl cinnamic acid methyl ester
- p-methoxycinnamic acid isoamyl ester (Neo Heliopan® E 1000)
- p-methoxycinnamic acid diethanolamine salt
- p-methoxycinnamic acid isopropyl ester
- 2-phenylbenzimidazole sulfonic acid and salts (Neo Heliopan® Hydro)
- 3-(4'-trimethylammonium) benzylidene bornan-2-one methyl sulfate
- beta-imidazole-4(5)-acrylic acid (urocanic acid)
- 3-(4'-sulfo)benzylidene bornan-2-one and salts
- 3-(4'-methyl benzylidene)-D,L-camphor (Neo Heliopan® MBC)
- 3-benzylidene-D,L-camphor
- N-[(2 and 4)-[2-(oxoborn-3-ylidene) methyl]benzyl] acrylamide polymer
- 4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb® HEB)
- benzylidene malonate polysiloxane (Parsol® SLX)
- glyceryl ethylhexanoate dimethoxycinnamate
- dipropylene glycol salicylate
- tris(2-ethylhexyl)-4,4',4"-(1,3,5-triazine-2,4,6-triyltriimino)tribenzoate (=2,4,6-trianilino-(p-carbo-2'-ethylhexyl-1'-oxy)-1,3,5-triazine) (Uvinul® T150)

Broadband filters which are preferably combined with one or more compounds of formula (I) in a preparation according to the present invention are selected from the group consisting of
- 2-ethylhexyl-2-cyano-3,3-diphenyl acrylate (Neo Heliopan® 303)
- ethyl-2-cyano-3,3'-diphenyl acrylate
- 2-hydroxy-4-methoxybenzophenone (Neo Heliopan® BB)
- 2-hydroxy-4-methoxybenzophenone-5-sulfonic acid
- dihydroxy-4-methoxybenzophenone
- 2,4-dihydroxybenzophenone
- tetrahydroxybenzophenone
- 2,2'-dihydroxy-4,4'-dimethoxybenzophenone
- 2-hydroxy-4-n-octoxybenzophenone
- 2-hydroxy-4-methoxy-4'-methyl benzophenone
- sodium hydroxymethoxybenzophenone sulfonate
- disodium-2,2'-dihydroxy-4,4'-dimethoxy-5,5'-disulfobenzophenone
- phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)
- 2,2'-methylene bis-(6-(2H-benzotriazol-2-yl)-4-1,1,3,3-tetramethyl butyl) phenol) (Tinosorb® M)
- 2,4-bis-[4-(2-ethylhexyloxy)-2-hydroxyphenyl]-1,3,5-triazine
- 2,4-bis-[{(4-(2-ethylhexyloxy)-2-hydroxy}phenyl]-6-(4-methoxyphenyl)-1,3,5-triazine (Tinosorb® S)
- 2,4-bis-[{(4-(3-sulfonato)-2-hydroxypropyloxy)-2-hydroxy}phenyl]-6-(4-methoxyphenyl)-1,3,5-triazine sodium salt
- 2,4-bis-[{(3-(2-propyloxy)-2-hydroxypropyloxy)-2-hydroxy}phenyl]-6-(4-methoxyphenyl)-1,3,5-triazine
- 2,4-bis-[{4-(2-ethylhexyloxy)-2-hydroxy}phenyl]-6-[4-(2-methoxyethyl carbonyl) phenylamino]-1,3,5-triazine
- 2,4-bis-[{4-(3-(2-propyloxy)-2-hydroxypropyloxy)-2-hydroxy}phenyl]-6-[4-(2-ethylcarboxyl) phenylamino]-1,3,5-triazine
- 2,4-bis-[{4-(2-ethylhexyloxy)-2-hydroxy}phenyl]-6-(1-methylpyrrol-2-yl)-1,3,5-triazine
- 2,4-bis-[{4-tris-(trimethylsiloxysilylpropyloxy)-2-hydroxy}phenyl]-6-(4-methoxyphenyl)-1,3,5-triazine
- 2,4-bis-[{4-(2"-methylpropenyloxy)-2-hydroxy}phenyl]-6-(4-methoxyphenyl)-1,3,5-triazine
- 2,4-bis-[{4-(1',1',1',3',5',5',5'-heptamethylsiloxy-2"-methylpropyloxy)-2-hydroxy}phenyl]-6-(4-methoxyphenyl)-1,3,5-triazine UV-A filters filters which are preferably combined with one or more compounds of formula (I) in a preparation according to the present invention are selected from the group consisting of
- 4-isopropyl dibenzoyl methane
- terephthalylidene dibornane sulfonic acid and salts (Mexoryl® SX)
- 4-t-butyl-4'-methoxydibenzoyl methane (avobenzone)/ (Neo Heliopan® 357)
- phenylene bis-benzimidazyl tetrasulfonic acid disodium salt (Neo Heliopan® AP)
- 2,2'-(1,4-phenylene)-bis-(1H-benzimidazole-4,6-disulfonic acid), monosodium salt
- 2-(4-diethylamino-2-hydroxybenzoyl) benzoic acid hexyl ester (Uvinul® A Plus)
- indanylidene compounds in accordance with DE 100 55 940 A1 (=WO 2002 038537 A1)

UV filters which are more preferably combined with one or more compounds of formula (I) in a preparation according to the present invention are selected from the group consisting of
- p-aminobenzoic acid
- 3-(4'-trimethylammonium) benzylidene bornan-2-one methyl sulfate
- salicylic acid homomenthyl ester (Neo Heliopan® HMS)
- 2-hydroxy-4-methoxybenzophenone (Neo Heliopan® 1313)
- 2-phenylbenzimidazole sulfonic acid (Neo Heliopan® Hydro)
- terephthalylidene dibornane sulfonic acid and salts (Mexoryl® SX)
- 4-tert-butyl-4'-methoxydibenzoyl methane (Neo Heliopan® 357)

3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene) methyl]benzyl] acrylamide polymer
p-methoxycinnamic acid-2-ethylhexyl ester (Neo Heliopan® AV)
p-aminobenzoic acid ethyl ester (25 mol) ethoxylated (INCI name: PEG-25 PABA)
p-methoxycinnamic acid isoamyl ester (Neo Heliopan® E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan® MBC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb® M)
phenylene bis-benzimidazyl tetrasulfonic acid disodium salt (Neo Heliopan® AP)
2,4-bis-[{(4-(2-ethylhexyloxy)-2-hydroxy}phenyl]-6-(4-methoxyphenyl)-1,3,5-triazine (Tinosorb® S)
benzylidene malonate polysiloxane (Parsol® SLX)
menthyl anthranilate (Neo Heliopan® MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

F. Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

G. Anti-Ageing Actives

In the context of the invention, anti-ageing or biogenic agents are, for example antioxidants, matrix-metalloproteinase inhibitrors (MMPI), skin moisturizing agents, glycosaminglycan stimulkators, anti-inflammatory agents, TRPV1 antagonists and plant extracts.

(i) Antioxidants. amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, sophora, pueraria, pinus, citrus, Phyllanthus emblica or St. John's wort, grape seeds, wheat germ, Phyllanthus emblica, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

(ii) Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1 (2H)-benzopyran, 3,4-dihydro-6-hydroxy-7-methoxy-2, 2-dimethyl-1(2H)-benzopyran, benzamidine hydrochloride, the cysteine proteinase inhibitors N-ethyl-malemide and epsilon-amino-n-caproic acid of the serin-protease inhibitors: phenylmethylsufonylfluoride, collhibin (company Pentapharm; INCI: hydrolysed rice protein), oenotherol (company Soliance; INCI: propylene glycol, aqua, Oenothera biennis root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

(III) Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

(iv) Glycosaminoglycan stimulators. Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, Alpinia galanga leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, Eriobotrya *japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, Alpinia galanga leaf extract and tetradecyl aminobutyroylvalylaminobutyric urea trifluoroacetate.

(v) Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, *arnica*, St John's wort, honeysuckle, rosemary, *Passiflora incarnata*, witch hazel, ginger or *Echinacea*; preferably selected from the group consisting of extracts or fractions from camomile, Aloe vera, oats, calendula, *arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

(vi) TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred. (vii) Botanical extracts. The compositions may also contain various extracts of plants, such as for example extracts of *Ginkgo biloba, Oleacea europensis, Glyzyrrhiza glabra, Vaccinium myrtillus, Tnfolium pratense, Litchi sinensis, Vitis, vinifera, Brassica oleracea, Punica granatum, Petroselinium crispurn, Centella asiatica, Passiflora incarnata, Medicago sativa, Melissa officinalis, Valeriana officinalis, Castanea sativa, Salix alba* and *Hapagophytum procumbens*.

H. Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy-)acetate, menthylpyroglutamate), menthylcarbonates (for example menthylpropyleneglycol-carbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)-amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [W523]), isopulegol or its esters (I-(–)-isopulegol, I-(–)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

I. Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

J. Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

K. Odour Absorbers and Antiperspirant Active Agents

Suitable odour absorbers are substances which are able to absorb and largely retain odourforming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

L. Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethyl-pentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

M. Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gel-Ian gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

N. Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

O. Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and flora mat.

P. Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preferred compositions according to the present inventions are selected from the group of products for treatment, protecting, care and cleansing of the skin and/or hair or as a makeup product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

INDUSTRIAL APPLICATION

In a preferred embodiment the compositions according to the present invention comprise the components in the following amounts:
(a) about 0.1 to about 5, preferably about 0.3 to about 3 and more preferably about 0.5% b.w. to about 2.5% b.w. menthone ketals of formula (I);
(b) about 99.9 to about 50, preferably about 95 to about 65 and more preferably about 80 to about 70% b.w. oil bodies and/or waxes;
(c) 0 to about 25, preferably about 1 to about 15 and more preferably about 4 to about 8% b.w. emulsifiers;
(d) 0 to about 25, preferably about 0.5 to about 10 and more preferably about 1 to about 5% b.w. active principles;
on condition that the amounts add—optionally together with water and additional ingredients—to 100% b.w.

The inventive compositions may contain water or are essentially free of water. Essentially free means that the amount of water is less than 2, preferably less than 1 and more preferably less than 0.5% b.w. calculated on the final product.

The compositions according to the invention may represent o/w or w/o or multiple o/w/o or w/o/w emulsion. They can be used as an intermediate or a final product for example in the form of a lotion, a cream or a stick.

Two other embodiments of the present invention relate to the use of menthone ketals according to formula (I) as stabilizers for cosmetic compositions and as additive able to improve the sensorial profile of cosmetic compositions.

EXAMPLES

Examples 1 to 3, Comparative Examples C1 to C3

O/W emulsions were prepared by heating a lipid phase A and an aqueous phase B separately to approximately 80° C. Then the aqueous phase B was added to the lipid phase A and mixed in an Ultra-Turrax for 2 minutes at 5.000 rpm. The emulsion thus obtained was allowed to cool down for 10 minutes using a vane stirrer at 150 rpm. Finally, the pH value was adjusted to about 8.0 by adding aqueous sodium hydroxide solution. The stability of the emulsions was determined using an analytical centrifuge of the LUMisizer® type (L.U.M. GmbH) which measures the change in transmission over time. The instability index is defined between 0 (very stable) and 1 (complete separation). The experiments were conducted at 25° C. with a speed of 2.500 rpm over 1.25 h corresponding to a storage time of about 1 month. The composition of the emulsions and the stability results are provided in Table 1. Examples 1 to 3 are according to the invention, Examples C1 to C3 serve for comparison.

TABLE 1

| | O/W emulsions comprising Emulsiphos ® | | | | | | |
|---|---|---|---|---|---|---|---|
| Phase | Compound | C1 | C2 | C3 | 1 | 2 | 3 |
| A | Potassium Cetyl Phosphate (and) Hydrogenated Palm Glycerides Emulsiphos ® PN 677660 | 2.0 | 2.0 | 2.0 | 2.0 | 2.0 | 2.0 |
| | Cetearyl Alcohol Lanette ® O | 0.5 | 0.5 | 0.5 | 0.5 | 0.5 | 0.5 |
| | Capric Caprylic Glycerides Myritol ® 312 | 10.0 | — | — | 10.0 | — | — |
| | Cetearyl Ethylhexanoate PCL Liquid 100 | — | 10.0 | — | — | 10.0 | — |
| | Soybean oil | — | — | 10.0 | — | — | 10.0 |
| | Menthone Glycerin Acetal (FEMA 3807) Frescolat ® MGA | — | — | — | 2.0 | 2.0 | 2.0 |
| | Dimethicone Abil ® 350 | 0.1 | 0.1 | 0.1 | 0.1 | 0.1 | 0.1 |
| B | Glycerol | 1.0 | 1.0 | 1.0 | 1.0 | 1.0 | 1.0 |
| | Water | | | Ad 100 | | | |
| | Instability index | 0.35 | 0.47 | 0.36 | 0.08 | 0.38 | 0.19 |

The examples and comparative examples clearly demonstrate that adding Menthone Glycerin Acetal (FEMA 3807) to the emulsions leads to less separation and improves the stability of the emulsion.

Examples 4 to 6, Comparative Examples C4 to C6

O/W emulsions were prepared according to the procedure explained for Examples 1 to 3 with the only exception that the pH value was adjusted to about 9.1. The stability of the emulsions was again determined using an analytical centrifuge of the LUMisizer® type (L.U.M. GmbH). The composition of the emulsions and the stability results are provided in Table 2. Examples 4 to 6 are according to the invention, Examples C4 to C6 serve for comparison.

TABLE 1

O/W emulsions comprising Dracorin ®

| Phase | Compound | C4 | C5 | C6 | 4 | 5 | 6 |
|---|---|---|---|---|---|---|---|
| A | Glyceryl Stearate (and) PEG-100 Stearate Dracorin ® 100 SEP | 3.5 | 3.5 | 3.5 | 3.5 | 3.5 | 3.5 |
|  | Cetearyl Alcohol Lanette ® O | 0.5 | 0.5 | 0.5 | 0.5 | 0.5 | 0.5 |
|  | Capric Caprylic Glycerides Myritol ® 312 | 10.0 | — | — | 10.0 | — | — |
|  | Cetearyl Ethylhexanoate PCL Liquid 100 | — | 10.0 | — | — | 10.0 | — |
|  | Soybean oil | — | — | 10.0 | — | — | 10.0 |
|  | Menthone Glycerin Acetal (FEMA 3807) Frescolat ® MGA | — | — | — | 2.0 | 2.0 | 2.0 |
|  | Dimethicone Abil ® 350 | 0.1 | 0.1 | 0.1 | 0.1 | 0.1 | 0.1 |
| B | Glycerol | 1.0 | 1.0 | 1.0 | 1.0 | 1.0 | 1.0 |
|  | Water | | | Ad 100 | | | |
|  | Instability index | 0.09 | 0.22 | 0.37 | 0.02 | 0.12 | 0.11 |

Also the second set of examples and comparative examples clearly demonstrates that adding Menthone Glycerin Acetal (FEMA 3807) to the emulsions leads to less separation and improves the emulsion stability.

Examples 7 to 9, Comparative Examples C7 to C9

O/W emulsions were prepared according to the procedure explained for Examples 1 to 3. The particle size distributions of o/w emulsions was measured using a Mastersizer Micro (Malvern) using the principle of laser diffraction.

Figure 1B:
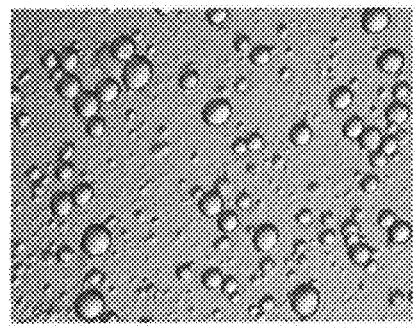
FIG. 1b is a picture of the emulsion of example 7 on a surface.
Figure 1C:
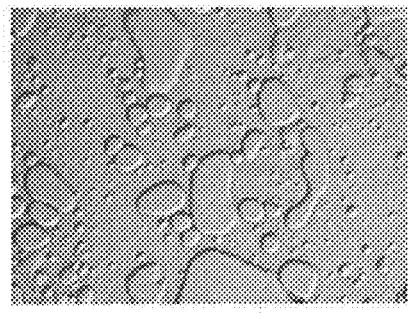
FIG. 1c is a picture of the emulsion of comparative example 7 on a surface.
Figure 2A:
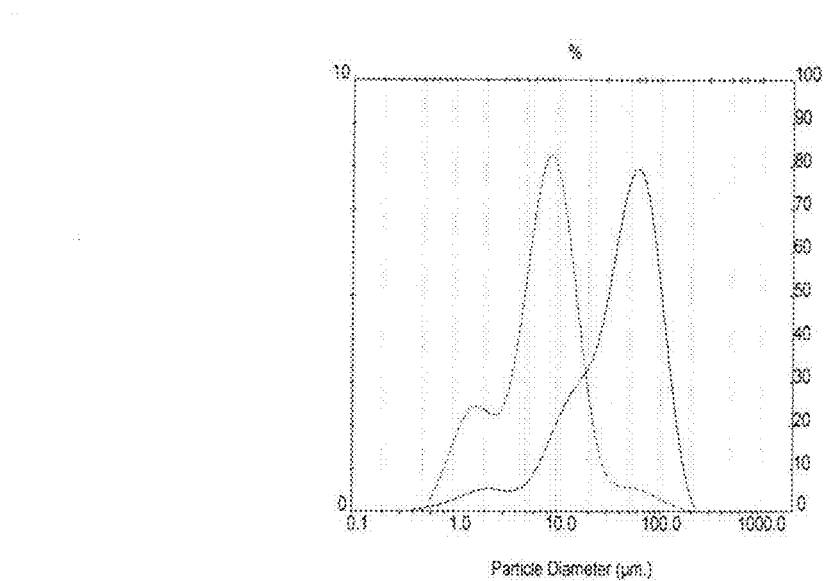
FIG. 2a is a graph of the particle diameter distribution of the emulsion of example 8 and comparative example C8 detailed in Tables 3 and 4.
Figure 2B:
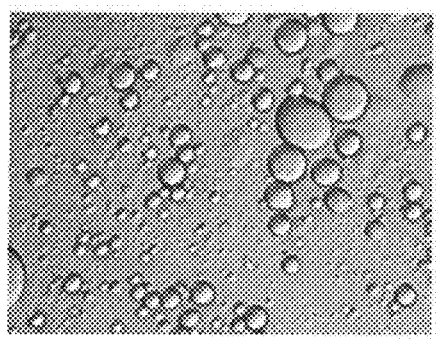
FIG. 2b is a picture of the emulsion of example 8 on a surface.
Figure 2C:
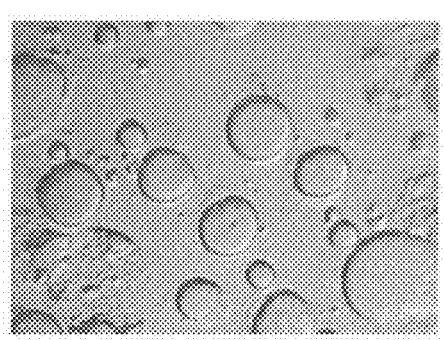
FIG. 2c is a picture of the emulsion of comparative example 8 on a surface.
Figure 3A:
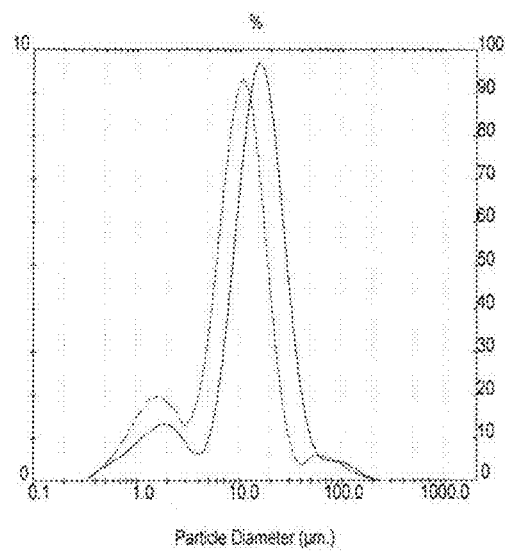
FIG. 3b is a picture of the emulsion of example 9 on a surface.
FIG. 3c is a picture of the emulsion of comparative example 9 on a surface.
Figure 3B:
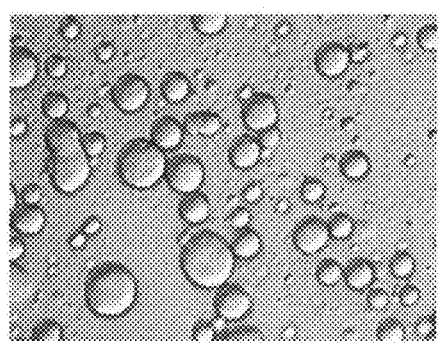
Figure 3C:
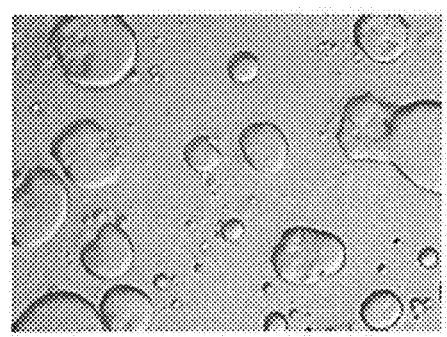

The compositions of the emulsions are provided in Table 3 and the results in table 4 and FIGS. 1, 2 and 3. Examples 7 to 8 are according to the invention, Examples C7 to C9 serve for comparison.

TABLE 4

Particle size distribution (all values in μm)

| Particle Size | C7 | 7 | C8 | 8 | C9 | 9 |
|---|---|---|---|---|---|---|
| D (v, 0.1) = 10% | 3.97 | 2.04 | 8.48 | 1.60 | 2.37 | 1.58 |
| D (v, 0.5) = 50% | 23.29 | 10.46 | 44.15 | 7.53 | 14.76 | 9.32 |
| D (v, 0.9) = 90% | 89.13 | 65.85 | 103.40 | 19.40 | 36.53 | 21.21 |

The index "v" refers to a volume based particle size distribution; all values were taken from the sum distribution $Q_r$. For example, the value 3.97 for C7 means that 10% of the particles show a particle size less than 3.97 μm and so on.

TABLE 3

O/W emulsions comprising Emulsiphos ®

| Phase | Compound | C7 | C8 | C9 | 7 | 8 | 9 |
|---|---|---|---|---|---|---|---|
| A | Potassium Cetyl Phosphate (and) Hydrogenated Palm Glycerides Emulsiphos ® PN 677660 | 2.0 | 2.0 | 2.0 | 2.0 | 2.0 | 2.0 |
|  | Cetearyl Alcohol Lanette ® O | 0.5 | 0.5 | 0.5 | 0.5 | 0.5 | 0.5 |
|  | Capric Caprylic Glycerides Myritol ® 312 | 10.0 | — | — | 10.0 | — | — |
|  | Cetearyl Ethylhexanoate PCL Liquid 100 | — | 10.0 | — | — | 10.0 | — |
|  | Soybean oil | — | — | 10.0 | — | — | 10.0 |
|  | Menthone Glycerin Acetal (FEMA 3807) Frescolat ® MGA | — | — | — | 2.0 | 2.0 | 2.0 |
|  | Dimethicone Abil ® 350 | 0.1 | 0.1 | 0.1 | 0.1 | 0.1 | 0.1 |
| B | Glycerol | 1.0 | 1.0 | 1.0 | 1.0 | 1.0 | 1.0 |
|  | Water | | | Ad 100 | | | |

As one can see, adding of Menthone Glycerin Acetal (FEMA 3807) shifts the maximum average particle size to smaller values and leads to more finely divided emulsions.

Example 10, Comparative Example C10

An emulsion (with an unperfumed base) was formulated with and without 2.0% b.w. Menthone Glycerin Acetal (FEMA 3807). Then, 0.5 g of both products were placed on a filter paper in a Petri dish and put into an air filled Sniffer bag. Before evaluation by a panel, the odour of an emulsion (reference) was introduced in the Sniffer bag. The panel (16 experienced experts) evaluated both samples regarding perfume and malodour intensity on a scale of 1=odourless to 9=very strong. The intensity of the reference is defined as 3. The results are reflected in Table 5 and show the arithmetic means of the tests. Example 10 is according to the invention, Example C10 for comparison.

TABLE 6

Masking of malodour

| Example | Product | Mean perfume intensity | Mean malodour intensity |
|---|---|---|---|
| Control | Reference | 1.00 | 3.00 |
| C10 | Sample without Menthone Glycerin Acetal (FEMA 3807) | 1.20 | 2.25 |
| 10 | Sample with Menthone Glycerin Acetal (FEMA 3807) | 2.67 | 1.80 |

Adjunction of Menthone Glycerin Acetal (FEMA 3807) to the product leads to a perfume intensity increase and a malodour reduction. Menthone Glycerin Acetal can be used for masking of the malodour of an emulsion.

Example 11, Comparative Example C11

Figure 4:
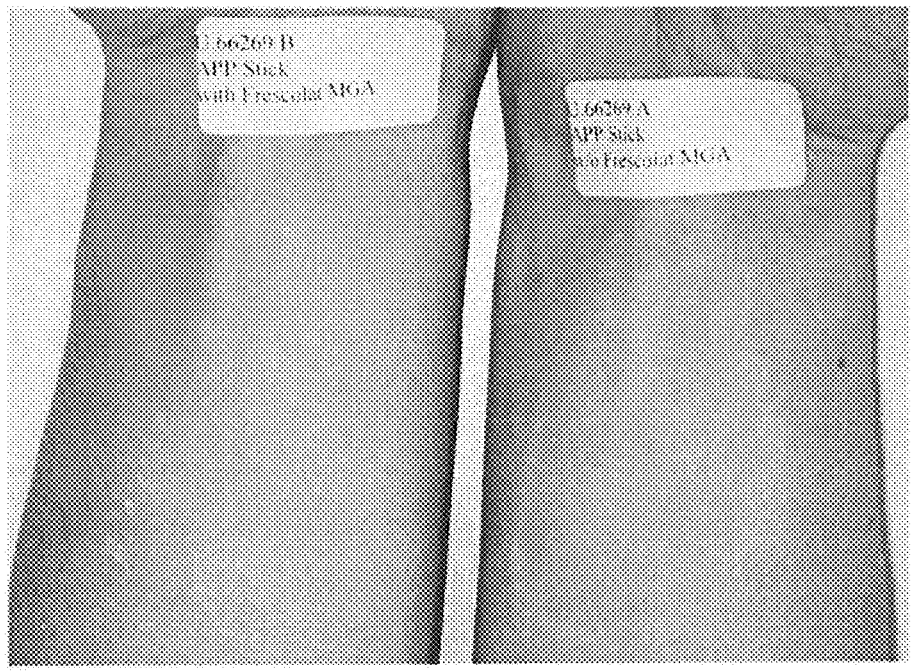
FIG. 4 is a picture of the level of abrasion on the skin by using an antiperspirant stick formulated with and without menthone glycerine acetal.
Figure 5:
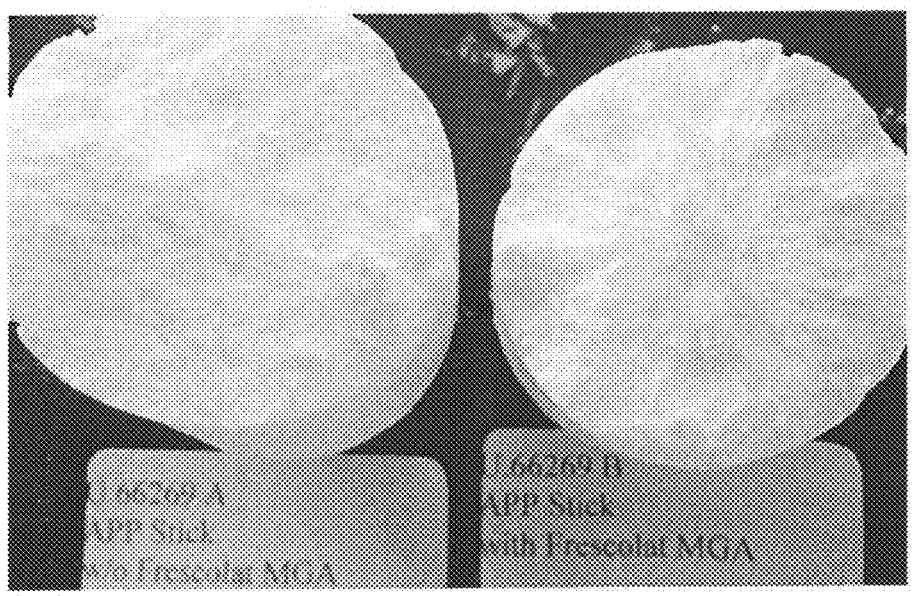
FIG. 5 is a picture of a broken antiperspirant stick formulated with and without menthone glycerine acetal.

An anti-perspirant (APP) stick was formulated with and without Menthone Glycerin Acetal (FEMA 3807) by blending a lipid and an alcoholic phase. The performance of both products was determined with respect to abrasion on the skin and appearance of the broken stick. The composition of the sticks and the results are provided in Table 6 and FIGS. 4 and 5.

TABLE 7

Performance APP sticks

| Phase | Compound | C11 | 11 |
|---|---|---|---|
| A | Glyceryl Stearate (and) PEG-100 Stearate Dracorin ® 100 SEP | 1.0 | 1.0 |
| | Cyclopentasiloxane | 52.7 | 50.7 |
| | PEG-150 Polyglycol 6000 S | 3.0 | 3.0 |
| | Stearyl Alcohol Lanette ® 18 | 20.0 | 20.0 |
| | Aluminium Chlorhydrate Locron ® P | 20.0 | 20.0 |
| | Talcum | 1.0 | 1.0 |
| | Silica Aerosil ® 200 | 1.5 | 1.5 |
| B | Dimethyl Phenylpropanol (and) Pentylene Glycol | 0.5 | 0.5 |
| | Menthone Glycerin Acetal (FEMA 3807) Frescolat ® MGA | — | 2.0 |
| | Water | Ad 100 | |
| | Abrasion on skin | dull, whitening | smooth, less dull, creamy |
| | Appearance of the broken stick | amorphous | crystalline |

Example 12, Comparative Example C12

Two emulsions were formulated with and without 2% Menthone Glycerin Acetal (FEMA 3807). The sensorial analysis of both products was realised during the same session in a room equipped with 12 cabins (with monitoring of the temperature and the humidity). The performance of both products was determined with respect to 14 descriptors. The composition of the emulsions and the results are provided in Table 7 and 8.

TABLE 7

Composition of the emulsions

| Phase | Compound | C12 | 12 |
|---|---|---|---|
| A | Potassium Cetyl Phosphate Hydrogenated Palm Glycerides Emulsiphos ® 677660 | 2 | 2 |
| | Cetearyl Alcohol Lanette ® O | 3 | 3 |
| | Ethylhexyl Isononanoate Dragoxat ® 89 | 7 | 7 |
| | Caprylic/Capric Triglyceride Neutral Oil | 5 | 5 |
| | Hydroxyethylacrylate/sodium acryloyldimethyl taurate copolymer (and) Polyisobutene (and) PEG-7 trimethylolpropane coconut ether Sepiplus ® S | 0.4 | — |
| B | Phenoxyethanol (and) Decylene Glycol (and) 1,2-Hexanediol SymOcide ® PS | 1 | 0.4 |
| | Aqua Water | 81.2 | 79.2 |
| | Xanthan Gum Keltrol ® CG-SFT | 0.4 | 0.4 |
| C | Menthone Glycerin Acetal (FEMA 3807) Frescolat ® MGA | — | 2 |

TABLE 8

Student test with matched products 12/C12

| Descriptors | 12 | C12 | Significance (%) |
|---|---|---|---|
| Opaque | 8.42-1.91 | 8.10-1.83 | 17.63 |
| White | 9.57-0.81 | 9.76-043 | 16.85 |
| Glossy | 9.33-0.91 | 9.09-0.99 | 28.76 |
| Fluid | 6.19-1.96 | 5.90-2.11 | 23.24 |
| High Pick | 2.42-2.06 | 1.85-1.79 | 2.64 |
| Slippery | 8.33 ± 2.06 | 8.76 ± 0.94 | 0.95 |
| Fresh | 5.52 ± 2.56 | 5.80 ± 2.13 | 44.6 |
| Whitening | 3.42 ± 2.44 | 4.14 ± 2.97 | 4.55 |
| Spreadable | 8.33 ± 1.15 | 8.19 ± 1.24 | 45.38 |
| Greasy | 4.57 ± 2.37 | 6.04 ± 1.93 | 1.08 |
| Sticky | 0.42 ± 0.59 | 1.04 ± 1.43 | 3.68 |
| Smooth | 7.14 ± 1.49 | 7.33 ± 1.62 | 70.51 |

TABLE 8-continued

Student test with matched products 12/C12

| Descriptors | 12 | C12 | Significance (%) |
|---|---|---|---|
| Absorption | 8.14 ± 1.76 | 8.19 ± 1.80 | 88.04 |
| Film forming | 0.23 ± 0.88 | 0.14 ± 0.47 | 64.96 |

The comparison between the two products show significant differences: the product according to the invention leads to a significant reduction of the descriptors "Greasy", "Sticky", "Slippery" and "Whitening" while it enhances "High Pick".

Example 13, Comparative Example C13

A Sunscreen was formulated with and without 1% Menthone Glycerin Acetal (FEMA 3807). The sensorial analysis of both products was realised during the same session in a room equipped with 12 cabins (with monitoring of the temperature and the humidity). The performance of both products was determined with respect to 14 descriptors. The composition of the emulsions and the results are provided in Table 9 and 10.

TABLE 9

Composition of the emulsions

| Phase | Compound | C12 | 12 |
|---|---|---|---|
| A | Potassium Cetyl Phosphate (and) Hydrogenated Palm Glycerides Emulsiphos ® | 2 | 2 |
|  | Cetyl Palmitate Cutina ® CP | 1 | 1 |
|  | Butyl Methoxydibenzoylmethane Neo Heliopan ® 357 | 3 | 3 |
|  | Ethylhexyl Salicylate Neo Heliopan ® OS | 5 | 5 |
|  | Octocrylene Neo Heliopan ® 303 | 8 | 8 |
|  | Homosalate Neo Heliopan ® HMS | 5 | 5 |
|  | Benzylidene Dimethoxydimethylin danone SymHelios ® 1031 | 0.5 | 0.5 |
|  | Ethylhexyl Isononanoate Dragoxat ® 89 | 2 | 2 |
|  | Stearyl Dimethicone Silcare ® | 1 | 1 |
|  | Caprylyl Methicone Silsoft ® 034 | 2 | 2 |
|  | Disodium EDTA Edeta ® BD | 0.1 | 0.1 |
|  | Tocopheryl Acetate Copherol ® 1250 | 0.5 | 0.5 |

TABLE 9-continued

Composition of the emulsions

| Phase | Compound | C12 | 12 |
|---|---|---|---|
|  | Xanthan Gum Keltrol ® CG-T | 0.2 | 0.2 |
|  | Acrylates/C10-30 Alkyl acrylate Crosspolymer Carbopol ® Ultrez 21 | 0.3 | 0.3 |
| B | Water | 46.25 | 45.25 |
|  | Phenylbenzimidazole Sulfonic Acid Neo Heliopan ® neutralized with Biotive L-Arginine | 12 | 12 |
|  | Glycerin | 3 | 3 |
|  | Arginine Biotive L-Arginine | 0.8 | 0.8 |
| C | Phenoxyethanol (and) Decylene Glycol (and) 1,2-Hexanediol SymOcide ® PS | 1.25 | 1.25 |
| D | Bisabolol Dragosantol ® 100 | 0.1 | 0.1 |
|  | Alcohol Denat. | 3 | 3 |
|  | Menthone Glycerin Acetate Frescolat ® MGA | — | 1 |
| E | Polyamide-5 Orgasol ® Caresse | 1 | 1 |
|  | Water, Glycerin (and) Beta-Glucan (and) 1,2-Hexanediol (and) Caprylyl Glycol SymGlucan ® | 2 | 2 |

TABLE 10

Student test with matched products 13/C13 (Cont.)

| Descriptors | 13 | C13 | Significance (%) |
|---|---|---|---|
| Opaque | 8.75-1.99 | 8.85-1.98 | 16.88 |
| White | 2.00-2.05 | 2.34-2.10 | 7.30 |
| Glossy | 8.85-1.18 | 8.80-1.10 | 66.68 |
| Fluid | 8.00-1.52 | 7.80-1.42 | 16.88 |
| High Pick | 1.95-1.63 | 1.90-1.65 | 77.20 |
| Slippery | 8.25-2.09 | 8.05-2.13 | 33.22 |
| Fresh | 5.70-2.34 | 5.60-2.18 | 72.53 |
| Whitening | 2.80-1.85 | 3.05-2.06 | 35.15 |
| Spreadable | 8.10-1.41 | 8.05-1.50 | 74.87 |
| Greasy | 4.00-2.86 | 4.85-3.18 | 4.76 |
| Sticky | 2.65-1.98 | 2.60-2.08 | 84.76 |
| Smooth | 5.30-2.17 | 5.45-2.16 | 50.59 |
| Absorption | 6.60-2.92 | 6.20-3.17 | 9.05 |
| Film forming | 1.75-2.33 | 1.80-2.62 | 85.33 |

The comparison between the two products show significant differences: the product according to the invention leads to a significant reduction of the descriptor "Greasy". This means that the inventive product reduces the greasy feeling of sun care lotions.

In the following Tables 11 and 12 formulation examples for various cosmetic compositions are presented.

TABLE 11

Examples for cosmetic compositions (water, preservatives ad 100 % b.w.)

| Composition (INCI) | A | B | C | D | E | F | G | H | I | J |
|---|---|---|---|---|---|---|---|---|---|---|
| Texapon ® NSO Sodium Laureth Sulfate | — | 30.0 | 30.0 | — | 25.0 | — | — | — | — | — |
| Plantacare ® 818 Coco Glucosides | — | 10.0 | — | — | 20.0 | — | — | — | — | — |
| Plantacare ® PS 10 Sodium Laureth Sulfate (and) Coco Glucosides | 22.0 | — | 5.0 | 22.0 | — | — | — | — | — | — |
| Dehyton ® PK 45 Cocamidopropyl Betaine | 15.0 | 10.0 | 15.0 | 15.0 | 20.0 | — | — | — | — | — |

TABLE 11-continued

Examples for cosmetic compositions (water, preservatives ad 100 % b.w.)

| Composition (INCI) | A | B | C | D | E | F | G | H | I | J |
|---|---|---|---|---|---|---|---|---|---|---|
| Emulgade ® SE<br>Glyceryl Sterate (and) Ceteareth 12/20 (and) Cetearyl Alcohol (and) Cetyl Palmitate | — | — | — | — | — | 5.0 | 5.0 | 4.0 | — | — |
| Eumulgin ® B1<br>Ceteareth-12 | — | — | — | — | — | — | — | 1.0 | — | — |
| Lameform ® TGI<br>Polyglyceryl-3 Isostearate | — | — | — | — | — | — | — | — | 4.0 | — |
| Dehymuls ® PGPH<br>Polyglyceryl-2 Dipolyhydroxystearate | — | — | — | — | — | — | — | — | — | 4.0 |
| Monomuls ® 90-O 18<br>Glyceryl Oleate | — | — | — | — | — | — | — | — | 2.0 | — |
| Cetiol ® HE<br>PEG-7 Glyceryl Cocoate | 2.0 | — | — | 2.0 | 5.0 | — | — | — | — | 2.0 |
| Cetiol ® OE<br>Dicaprylyl Ether | — | — | — | — | — | — | — | — | 5.0 | 6.0 |
| Cetiol ® PGL<br>Hexyldecanol (and) Hexyldecyl Laurate | — | — | — | — | — | — | — | 3.0 | 10.0 | 9.0 |
| Cetiol ® SN<br>Cetearyl Isononanoate | 1.0 | — | — | 0.5 | — | 3.0 | 3.0 | — | — | — |
| Cetiol ® V<br>Decyl Oleate | — | 1.0 | — | — | 0.5 | 3.0 | 3.0 | — | — | — |
| Myritol ® 318<br>Coco Caprylate Caprate | — | — | 1.0 | — | — | — | — | 3.0 | 5.0 | 5.0 |
| Bees Wax | — | — | — | 0.5 | 0.5 | — | — | — | 7.0 | 5.0 |
| Nutrilan ® Elastin E20<br>Hydrolyzed Elastin | — | — | — | — | — | 2.0 | — | — | — | — |
| Nutrilan ® 1-50<br>Hydrolyzed Collagen | — | — | — | — | 2.0 | — | 2.0 | — | — | — |
| Gluadin ® AGP<br>Hydrolyzed Wheat Gluten | 0.5 | 0.5 | 0.5 | — | — | — | — | 0.5 | — | — |
| Gluadin ® WK<br>Sodium Cocoyl Hydrolyzed Wheat Protein | 2.0 | 2.0 | 2.0 | 2.0 | 5.0 | — | — | — | 0.5 | 0.5 |
| Euperlan ® PK 3000 AM<br>Glycol Distearate (and) Laureth-4 (and) Cocamidopropyl Betaine | 5.0 | — | — | 5.0 | — | — | — | — | — | — |
| Arlypon ® F<br>Laureth-2 | — | — | — | — | — | — | — | — | — | — |
| Hydagen ® CMF<br>Chitosan | 1.0 | 1.0 | 1.0 | 1.0 | 1.0 | 1.0 | 1.0 | 1.0 | 1.0 | 1.0 |
| Frescolat MGA<br>Menthone Glyceryl Acetal | 1.0 | 1.0 | 1.0 | 1.0 | 1.0 | 1.0 | 1.0 | 1.0 | 1.0 | 1.0 |
| Glycerin (86 Gew. -% ig) | — | — | — | — | — | 3.0 | 3.0 | 5.0 | 5.0 | 3.0 |

A-E = shower lotion,
F = soft creme,
G, H = moisturizing creme,
I, J = night creme

TABLE 12

Examples for cosmetic compositions (water, preservatives ad 100% b.w.)

| Composition (INCI) | K | L | M | N | O | P | Q | R | S | T |
|---|---|---|---|---|---|---|---|---|---|---|
| Dehymuls ® PGPH<br>Polyglyceryl-2 Dipolyhydroxystearate | 4.0 | 3.0 | — | 5.0 | — | — | — | — | — | — |
| Lameform ® TGI<br>Polyglyceryl-3 Diisostearate | 2.0 | 1.0 | — | — | — | — | — | — | — | — |
| Emulgade ® PL 68/50<br>Cetearyl Glucoside (and) Cetearyl Alcohol | — | — | — | — | 4.0 | — | — | — | 3.0 | — |
| Eumulgin ® B2<br>Ceteareth-20 | — | — | — | — | — | — | — | 2.0 | — | — |
| Tegocare ® PS<br>Polyglyceryl-3 Methylglucose Distearate | — | — | 3.0 | — | — | — | 4.0 | — | — | — |
| Eumulgin VL 75<br>Polyglyceryl-2 Dipolyhydroxystearate (and) Lauryl Glucoside (and) Glycerin | — | — | — | — | — | 3.5 | — | — | 2.5 | — |
| Bees Wax | 3.0 | 2.0 | 5.0 | 2.0 | — | — | — | — | — | — |
| Cutina ® GMS<br>Glyceryl Stearate | — | — | — | — | 2.0 | 4.0 | — | — | 4.0 | — |
| Lanette ® O<br>Cetearyl Alcohol | — | — | 2.0 | — | 2.0 | 4.0 | 2.0 | 4.0 | 4.0 | 1.0 |
| Antaron ® V 216<br>PVP/Hexadecene Copolymer | — | — | — | — | — | 3.0 | — | — | — | 2.0 |

TABLE 12-continued

Examples for cosmetic compositions (water, preservatives ad 100% b.w.)

| Composition (INCI) | K | L | M | N | O | P | Q | R | S | T |
|---|---|---|---|---|---|---|---|---|---|---|
| Myritol ® 818 Cocoglycerides | 5.0 | — | 10.0 | — | 8.0 | 6.0 | 6.0 | — | 5.0 | 5.0 |
| Finsolv ® TN C12/15 Alkyl Benzoate | — | 6.0 | — | 2.0 | — | — | 3.0 | — | — | 2.0 |
| Cetiol ® J 600 Oleyl Erucate | 7.0 | 4.0 | 3.0 | 5.0 | 4.0 | 3.0 | 3.0 | — | 5.0 | 4.0 |
| Cetiol ® OE Dicaprylyl Ether | 3.0 | — | 6.0 | 8.0 | 6.0 | 5.0 | 4.0 | 3.0 | 4.0 | 6.0 |
| Mineral Oil | — | 4.0 | — | 4.0 | — | 2.0 | — | 1.0 | — | — |
| Cetiol ® PGL Hexadecanol (and) Hexyldecyl Laurate | — | 7.0 | 3.0 | 7.0 | 4.0 | — | — | — | 1.0 | — |
| Bisabolol | 1.2 | 1.2 | 1.2 | 1.2 | 1.2 | 1.2 | 1.2 | 1.2 | 1.2 | 1.2 |
| Frescolat ® MGA Menthone Glyceryl Acetal | 1.0 | 1.0 | 1.0 | 1.0 | 1.0 | 1.0 | 1.0 | 1.0 | 1.0 | 1.09 |
| Hydagen ® CMF Chitosan | 1.0 | 1.0 | 1.0 | 1.0 | 1.0 | 1.0 | 1.0 | 1.0 | 1.0 | 1.0 |
| Copherol ® F 1300 Tocopherol/Tocopheyl Acetate | 0.5 | 1.0 | 1.0 | 2.0 | 1.0 | 1.0 | 1.0 | 2.0 | 0.5 | 2.0 |
| Neo Heliopan ® Hydro Sodium Phenylbenzimidazole Sulfonate | 3.0 | — | — | 3.0 | — | — | 2.0 | — | 2.0 | — |
| Neo Heliopan ® 303 Octocrylene | — | 5.0 | — | — | — | 4.0 | 5.0 | — | — | 10.0 |
| Neo Heliopan ® BB Benzophenone-3 | 1.5 | — | — | 2.0 | 1.5 | — | — | — | 2.0 | — |
| Neo Heliopan ® E 1000 Isoamyl p-Methoxycinnamate | 5.0 | — | 4.0 | — | 2.0 | 2.0 | 4.0 | 10.0 | — | — |
| Neo Heliopan ® AV Octyl Methoxycinnamate | 4.0 | — | 4.0 | 3.0 | 2.0 | 3.0 | 4.0 | — | 10.0 | 2.0 |
| Uvinul ® T 150 Octyl Triazone | 2.0 | 4.0 | 3.0 | 1.0 | 1.0 | 1.0 | 4.0 | 3.0 | 3.0 | 3.0 |
| Zinc Oxide | — | 6.0 | 6.0 | — | 4.0 | — | — | — | — | 5.0 |
| Titanium Dioxide | — | — | — | — | — | — | — | 5.0 | — | — |
| Glycerin (86 Gew.-% ig) | 5.0 | 5.0 | 5.0 | 5.0 | 5.0 | 5.0 | 5.0 | 5.0 | 5.0 | 5.0 |

K-N = w/o sun care creme or lotion,
O-T: o/w sun care creme or lotion

The invention claimed is:

1. A cosmetic composition, comprising
   (a) 0.3% to about 3.0% b.w. menthone compounds of formula (Ia) and/or (Ib)

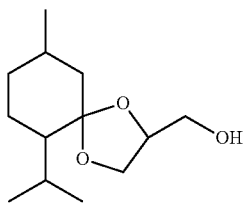

(Ia)

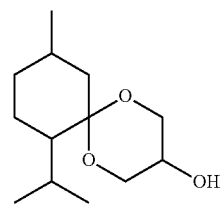

(Ib)

and
   (b) 95% to about 65% b.w. natural waxes which are selected from the group consisting of candelilla wax, carnauba wax, Japan wax, esparto grass wax, cork wax, guaruma wax, rice oil wax, sugar cane wax, ouricury wax, montan wax, beeswax, shellac wax, spermaceti, lanolin, uropygial fat, ceresine, ozocerite, petrolatum, paraffin waxes and microwaxes, montan ester waxes, sasol waxes, hydrogenated jojoba waxes, polyalkylene waxes, polyethylene glycol waxes, and mixtures thereof, and
   (c) 1 to 15% b.w. emulsifiers, and
   (d) 0.5 to 10% b.w. active principles
   wherein the emulsifiers are selected from the group consisting of non-ionic, anionic, cationic, or amphoteric emulsifiers and their mixtures, and
   on condition that the amounts add—together with water and additional ingredients—to 100% b.w.

2. The cosmetic composition of claim 1, wherein compound (a) is L-Menthone glycerol ketal (FEMA GRAS 3807) and DL-Menthone Glycerol Ketal (FEMA GRAS 3808) or their mixture.

3. The cosmetic composition of claim 1, wherein the product is a lotion, a cream or a stick.

4. The cosmetic composition of claim 1 wherein the emulsion is in a form selected from the group consisting of a PIT emulsion, a Pickering emulsion, a micro-emulsion, a nano-emulsion, a solution in fatty acids or fatty acid esters, a solution in silicone oil, a créme, a milk, a gel, a foam, a spray, an impregnating solution for cosmetic wipes, a detergent, a bath product, an effervescent preparation, a skin care product, a pencil, a stick, a roll-on, a pump, an aerosol, a deodorant and/or antiperspirant, a mouthwash, a mouthrinse, a foot care product, an insect repellant, a sunscreen, an aftersun preparation, a shaving product, a depilatory agent, a hair care product, an eye care product, make-up, make-up remover and a baby product.

5. A cosmetic composition, comprising
(a) 0.3% to about 3.0% b.w. menthone compounds of formula (Ia) and/or (Ib)

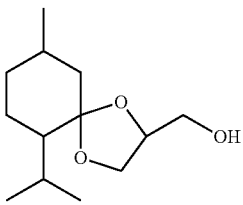
(Ia)

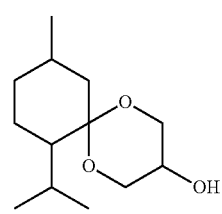
(Ib)

and
(b) 95% to about 65% b.w. Guerbet carbonates based on fatty alcohols having 8 to 10 carbon atoms,
(c) 1 to 15% b.w. emulsifiers, and
(d) 0.5 to 10% b.w. active principles
wherein the emulsifiers are selected from the group consisting of non-ionic, anionic, cationic, or amphoteric emulsifiers and their mixtures, and
on condition that the amounts add—together with water and additional ingredients—to 100% b.w.

6. A method for
i) improving stability of cosmetic compositions, or
ii) for reducing average particle size of droplets in an emulsion, or
iii) for improving the sensorial profile of a deodorant stick or emulsion,
said method comprising the steps of:
providing menthone ketals of formula (Ia) and/or (Ib)

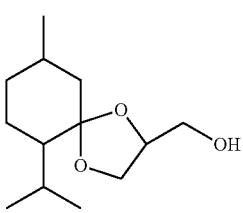
(Ia)

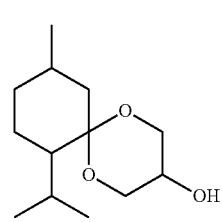
(Ib)

to a cosmetic composition to obtain a cosmetic composition which comprises
(a) 0.3% to about 3.0% b.w. menthone compounds of formula (Ia) and/or (Ib), and
(b) 95% to about 65% b.w natural waxes which are selected from the group consisting of candelilla wax, carnauba wax, Japan wax, esparto grass wax, cork wax, guaruma wax, rice oil wax, sugar cane wax, ouricury wax, montan wax, beeswax, shellac wax, spermaceti, lanolin, uropygial fat, ceresine, ozocerite, petrolatum, paraffin waxes and microwaxes, montan ester waxes, sasol waxes, hydrogenated jojoba waxes, polyalkylene waxes, polyethylene glycol waxes, and mixtures thereof, and
(c) 1 to 15% b.w. emulsifiers, and
(d) 0.5 to 10% b.w. active principles,
wherein the emulsifiers are selected from the group consisting of non-ionic, anionic, cationic, or amphoteric emulsifiers and their mixtures, and
on condition that the amounts add—together with water and additional ingredients—to 100% b.w.

7. A method for masking malodour in a cosmetic composition having an intrinsic fatty smell, the method comprising the steps of
adding menthone ketals of formula (Ia) and/or (Ib)

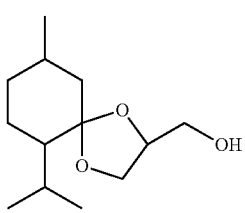
(Ia)

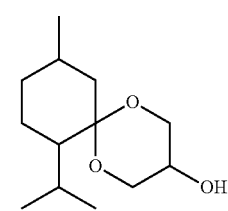
(Ib)

to a cosmetic composition to form a cosmetic composition having an intrinsic fatty smell, wherein the addition of the menthone ketals of formula (Ia) and/or (Ib) results in reduction of malodour in the cosmetic composition and wherein the cosmetic composition comprises
(a) 0.3% to about 3.0% b.w. menthone compounds of formula (Ia) and/or (Ib), and
(b) 95% to about 65% b.w natural waxes which are selected from the group consisting of candelilla wax, carnauba wax, Japan wax, esparto grass wax, cork wax, guaruma wax, rice oil wax, sugar cane wax, ouricury wax, montan wax, beeswax, shellac wax, spermaceti, lanolin, uropygial fat, ceresine, ozocerite, petrolatum, paraffin waxes and microwaxes, montan ester waxes, sasol waxes, hydrogenated jojoba waxes, polyalkylene waxes, polyethylene glycol waxes, and mixtures thereof, and
(c) 1 to 15% b.w. emulsifiers, and
(d) 0.5 to 10% b.w. active principles,
wherein the emulsifiers are selected from the group consisting of non-ionic, anionic, cationic, or amphoteric emulsifiers and their mixtures, and
on condition that the amounts add—together with water and additional ingredients—to 100% b.w.

* * * * *